(12) United States Patent
Lebel et al.

(10) Patent No.: US 7,130,038 B2
(45) Date of Patent: Oct. 31, 2006

(54) METHOD AND APPARATUS FOR OPTICAL FILM MEASUREMENTS IN A CONTROLLED ENVIRONMENT

(75) Inventors: Richard J. Lebel, Williston, VT (US); Fredrik Maurer, Valhalla, NY (US); Paul H. Smith, Jr., Essex Junction, VT (US); Theodore G. Van Kessel, Millbrook, NY (US); Hematha K. Wickramasinghe, Chappaqua, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 11/216,101

(22) Filed: Sep. 1, 2005

(65) Prior Publication Data

US 2005/0286056 A1 Dec. 29, 2005

Related U.S. Application Data

(62) Division of application No. 10/310,759, filed on Dec. 6, 2002, now Pat. No. 6,967,715.

(51) Int. Cl.
*G01N 21/00* (2006.01)

(52) U.S. Cl. ............... 356/237.3; 356/237.2; 451/6

(58) Field of Classification Search ............ None
See application file for complete search history.

(56) References Cited

U.S. PATENT DOCUMENTS

| 5,637,029 | A | 6/1997 | Lehane |
| 6,319,093 | B1 | 11/2001 | Lebel et al. |
| 6,676,766 | B1 * | 1/2004 | Harano et al. ............ 438/906 |

\* cited by examiner

*Primary Examiner*—Michael P. Stafira
*Assistant Examiner*—Juan D. Valentin, II
(74) *Attorney, Agent, or Firm*—Stephen C. Kaufman, Esq; McGinn IP Law Group, PLLC

(57) ABSTRACT

An optical probe (and method) for measuring a surface in an environment containing a first substance, includes a light source for transmitting a light onto an area of the surface to obtain a measurement, a source of the first substance including one of a fluid and a gas for displacing a second substance from an area of the surface receiving the light, and a measuring device for receiving the light being reflected from the surface and for determining a measurement of the surface based upon the reflected light.

18 Claims, 2 Drawing Sheets

METHOD AND APPARATUS FOR OPTICAL FILM MEASUREMENTS IN A CONTROLLED ENVIRONMENT

The present Application is a Divisional Application of U.S. patent application Ser. No. 10/310,759, filed on Dec. 6, 2002, now U.S. Pat. No. 6,967,715.

BACKGROUND OF THE INVENTION

1. Field of the Invention

The present invention generally relates to optical measurements in a controlled environment. In particular, the present invention relates to an air coupled probe for optical film measurements in a moist aqueous environment.

2. Description of the Related Art

Optical film thickness measurements are performed routinely in the semiconductor fabrication and machining processes to control film deposition and removal processes. In particular, chemical mechanical polishing (CMP) is used in semiconductor fabrication. In the CMP process, wafers containing thin films are polished in an aqueous environment to planarize the surface. The CMP process is often performed as a multistep process during which the wafers being polished are kept wet. It is desirable to measure the thickness of the material so that the wafers are not over polished and so that surface planarity may be gauged. Presently, the wafers are first removed from the polishing tool, cleaned and dried before film measurements may be made. Thus, there is a significant delay between the polishing operation and the measurement of the results of the polishing operation.

There is also excessive handling of the wafers between the polishing tool and the measurement area which results in significant cost.

It is desirable to measure the film thickness as soon as possible after the polishing process. However, this has not been practical to measure the film thickness immediately after the polishing process, because the wafer is placed in a rinsing tank and rinsed with water. It is very difficult to obtain an accurate thin film measurement in this environment.

Optical measurements are most easily performed in air. In other words, the optical beam used to make the measurement should pass through air directly to the surface film being measured.

SUMMARY OF THE INVENTION

In view of the above objects, an exemplary embodiment of the invention provides a vortex of air which displaces the water away from the area being measured. The optical signal in this case has a significantly higher contrast than it would if performed in a water environment due to the larger optical index mismatch. This is especially true for measurement of silicon dioxide thin films. In an air-SiO2 system, the index mismatch is 1:1.45 as opposed to 1.33:1.45 in the water-SiO2 system. This translates in practice to about a five times improvement in optical signal contrast.

Additionally, since the wafers are wet and in a moist environment, but not totally immersed all of the time, the environment is non-uniform. A uniform known measurement environment is assured using the invention. An exemplary embodiment of the invention completely dries the surface of the film and removes any remaining mist, fog, or any other source of moisture from the area being measured.

In accordance with a first aspect of the invention, an optical probe for measuring a surface in an environment containing a first substance includes a light source for transmitting a light onto an area of a surface to obtain a measurement and a source of the first substance including one of a fluid and a gas for displacing a second substance from the area of the surface receiving the light.

In accordance with a second aspect of the invention, a method of measuring a surface in an environment containing a first substance includes displacing a second substance with a first substance including one of a fluid and a gas from an area of the surface; transmitting a light onto the area of the surface to obtain the surface measurement; and receiving light from the surface to obtain the measurement.

In accordance with yet a third aspect of the invention, the method may further include providing the results of the measurement to a polisher which performed the polishing process.

In accordance with one exemplary embodiment of the invention a probe is constructed for the purpose of performing air-coupled optical film measurements (surface film thickness of silicon dioxide in particular) in moist aqueous environments. The probe is particularly useful in the rinse area of chemical mechanical polishers to monitor and control the silicon dioxide film planarization process during semiconductor and thin film head manufacturing.

This embodiment of the probe includes a high pressure vortex air jet that rapidly clears both the surface containing the films to be measured and the window of the probe itself, thus enabling the passage of a measurement beam through air to the surface being tested.

Conventional thin film measurements were required to be taken after the rinse area of a chemical mechanical polisher and any feedback to the polisher was delayed. With an exemplary embodiment of the invention, feedback to the polisher occurs much earlier in the manufacturing process. The invention enables thin film measurements in a rinse tank which immediately follows the polishing process.

In addition to improving the feedback control loop characteristics, measurements performed in accordance with the invention have been shown to improve polish cycle time by at least 25%.

Other embodiments of the invention may operate in any environment in which the probe is able to provide a known substance to displace other fluid substances from the measuring environment. In one exemplary embodiment the probe operates in a degreasing environment and displaces any degreaser from the measuring environment before taking optical measurements.

Exemplary embodiments of the invention do not require handling and significantly reduce the cost of conventional systems. Additionally, exemplary embodiments of the invention are inexpensive to implement and may take advantage of existing part handling equipment. For example, the wafer is already chucked in the polishing tool and the wafer does not need to be removed from this chuck for exemplary embodiments of this invention.

BRIEF DESCRIPTION OF THE DRAWINGS

The foregoing and other purposes, aspects and advantages will be better understood from the following detailed description of an exemplary embodiment of the invention with reference to the drawings, in which.

DETAILED DESCRIPTION OF PREFERRED EMBODIMENTS OF THE INVENTION

Figure 1:
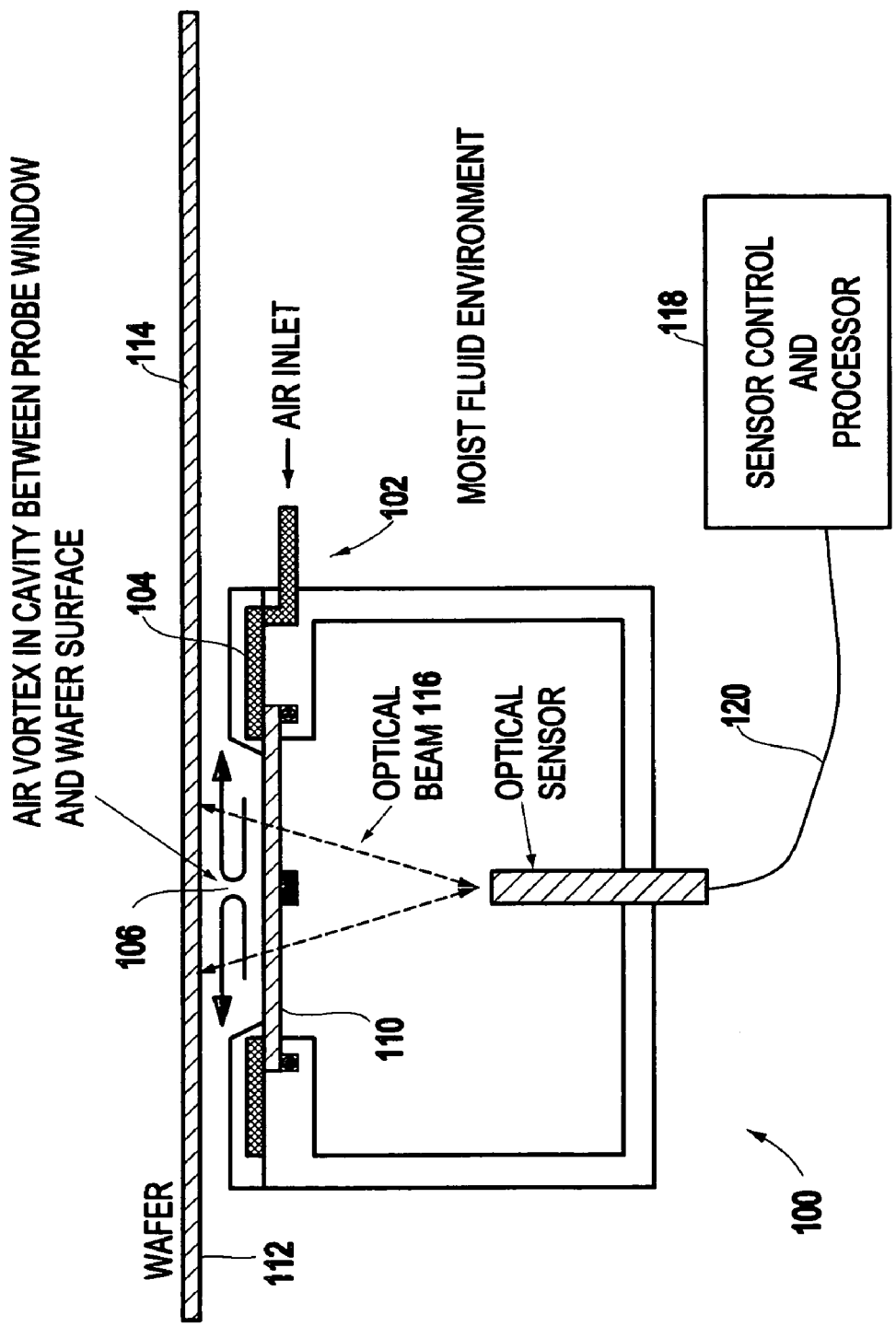
FIG. 1 shows a cross-sectional side view of one exemplary embodiment of a probe 100 in accordance with the present invention.
Figure 2:
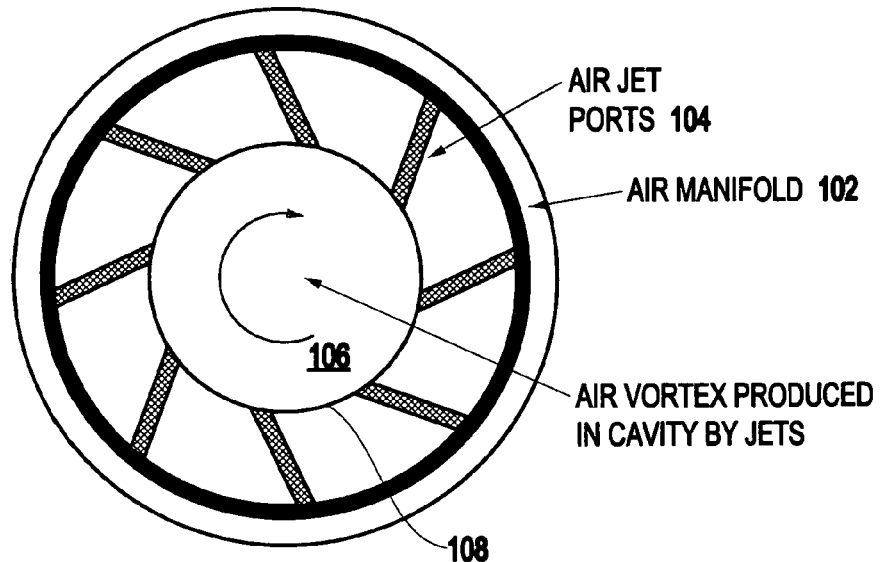
FIG. 2 shows a top view of the probe 100 of FIG. 1.

FIG. 1 illustrates the construction of an exemplary embodiment of a probe 100 in accordance with the present invention. As shown in the Figure, the probe 100 is operating in a moist fluid environment. The moist fluid environment may include any fluid or substance through which the probe 100 penetrates to a surface 112 to be measured. One example of a substance is water.

Air is introduced into a manifold 102 containing multiple jet nozzles 104 which direct the airflow into a vortex 106 in a cavity area 108 between a probe window 110 and a surface 112 of a wafer 114 containing the surface film to be measured.

The air-vortex 106 created by the air from the nozzles 104 displaces any moisture from the window 110 and the surface 112 of the wafer 114 and blows it to the side. The probe 100 is held in place in a mount (not shown) such that it is in close proximity (e.g., preferably with a gap of about 0.5 mm) to the wafer 114.

An optical beam 116 is emitted from a fiber (not shown) in the probe 100 and passes through the air to the surface film and back multiple times ultimately returning to the fiber from which it came. The resulting optical interference signal is transferred from the probe 100 to a spectrometer 118 via a fiber 120, analyzed into its component frequencies, digitized and finally analyzed by computer (not shown) such that the film thickness is computed from the interference signal using established mathematical methods which are well known to those of ordinary skill in the art.

In an exemplary method of using the probe 100 in accordance with the invention, wafers 114 are polished and moved to a rinse area (not shown) of the polisher (not shown) while being held in a chuck (not shown). The wafers 114 are rinsed with jets of water in the rinse area and allowed to remain on the chuck there for a brief period of time, such as about 10 seconds, while the air jets 104 of the probe 100 are activated. During this time, air vortex 106 clears substantially all surface moisture from the wafer area being measured and the interference signal is measured. The wafer 114 is then returned to the polisher (not shown) for additional planarization or removed from the tool to be cleaned and dried.

Figure 3:
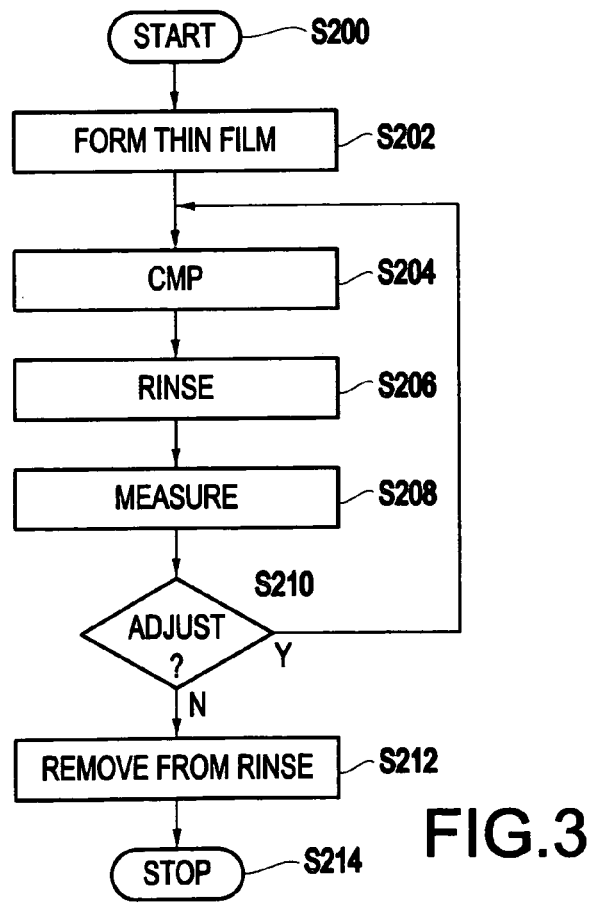
FIG. 3 shows a flowchart of one exemplary method of feedback control in accordance with the invention.

FIG. 3 shows a flowchart which illustrates one exemplary method of providing a feedback control loop using an exemplary embodiment of the invention. This feedback control loop significantly reduces the delay of conventional systems between the time when the polishing operation finishes and when a measurement of the results of that polishing operation is taken.

The process starts at step S200 and continues to step S202. In step S202, the wafer 114 is formed in accordance with conventional methods. Then, the wafer 114 is transported to a chemical mechanical polisher (not shown) where the surface 112 of the wafer 114 is planarized in step S204. The wafer 114 is then transported to a rinse tank (not shown) and rinsed to clear debris from the surface 112 of the polished wafer 114 in step S206. Then an exemplary embodiment of a probe 100 in accordance with the invention is positioned adjacent the surface 112 of the wafer 114 and air is supplied to displace the moisture from the area of the film being measured and a light beam 116 based measurement is take in step S208.

In step S210, a determination is made as to whether the polisher requires adjustment. If, in step S210, it is determined that the polisher requires adjustment, an error signal is sent back to the polisher and the polisher is adjusted accordingly. Additionally, the wafer 114 may also be returned to the polisher in step S204, if additional polishing is required.

If, in step S210, it is determined that no adjustment is required, then the process continues to step S212. In step S212, the wafer 114 is removed from the rinse area and continues along with conventional processing in step S214.

In contrast to the present invention, steps S208 and S210 could not be performed prior to step S212 using conventional methods. Thus, with an exemplary embodiment of the invention, feedback control of the polisher may be made much earlier and while the wafer 114 is still close to the polisher if additional polishing is required.

Moreover, the rinsing and measurement steps may be performed in the same chamber. That is, the wafer need not be removed from the rinsing chamber in order to measure the surface film thickness.

While the above description of exemplary embodiments related to an embodiment which provided air to displace water, it is to be understood that a probe could provide any substance in a gas or fluid form to displace any other substance or debris such that the environment within which the optical measurement is being taken acquires known optical qualities. For example, it is understood that another exemplary embodiment of the invention could be used in a degreaser, where air displaces a degreasing solution.

Additionally, while the exemplary embodiments described above generally refer to interference measurements between incident light waves and reflected light waves, those skilled in the art understand that any form of reflectance or transmissive spectrum analysis may be used and still form a part of the invention. For example, absorptive and/or transmissive properties of the wafer media may be measured to determine surface composition, thickness and/or roughness.

While the invention has been described in terms of several exemplary embodiments, those skilled in the art will recognize that the invention can be practiced with modification within the spirit and scope of the appended claims.

What is claimed is:

1. An optical probe for measuring a surface in an environment containing a first substance, comprising:
    a light source for transmitting a light onto an area of said surface to obtain a measurement;
    a source of said first substance including one of a fluid and a gas for displacing a second substance from said area of said surface receiving said light; and
    a measuring device for receiving said light being reflected from said surface and for determining a measurement of said surface based upon said reflected light,
    wherein said source of said first substance comprises a vortex.

2. The probe of claim 1, wherein said second substance comprises water.

3. The probe of claim 1, wherein said source of said first substance comprises at least one port.

4. The probe of claim 1, wherein said second substance comprises a degreaser.

5. The probe of claim 1, further comprising a processor for determining the results of said measurement.

6. The probe of claim 5, wherein said processor determines the thickness of said surface using said measurement.

7. The probe of claim 6, wherein said processor determines the composition of said surface using said measurement.

8. The probe of claim 1, wherein said source comprises air jets.

9. The probe of claim 1, wherein said source comprises an air manifold.

10. A method of measuring a surface in an environment containing a first substance, comprising:
   displacing a second substance with said first substance including one of a fluid and a gas from an area of said surface;
   transmitting a light onto said area of said surface to obtain said surface measurement; and
   receiving light from said surface to obtain said measurement,
   wherein said first substance is provided in a vortex.

11. The method of claim 10, wherein said second substance comprises water.

12. The method of claim 10, wherein a source of said first substance comprises at least one port.

13. The method of claim 10, wherein said second substance comprises a degreaser.

14. The method of claim 10, further comprising providing the results of said measurement to a polisher which performed the polishing process.

15. The method of claim 10, further comprising determining the thickness of said surface using the results of said measurement.

16. The method of claim 10, further comprising determining the composition of said surface using the results of said measurement.

17. An optical measurement system for measuring a surface in an environment containing a first substance comprising:
   a light source for transmitting a light onto an area of said surface to obtain a measurement;
   a source of said first substance including one of a fluid and a gas for displacing a second substance from said area of said surface receiving said light;
   a device for receiving said light being reflected from said surface and for outputting a signal; and
   a processor for determining a measurement of said surface based upon said signal,
      wherein said source of said first substance comprises a vortex.

18. A method of polishing a surface of a wafer, comprising:
   polishing said surface of said wafer in an environment containing a first substance;
   displacing said first substance with a second substance including one of a fluid and a gas from an area of said surface;
   transmitting a light onto said area of said surface to obtain a surface measurement regarding said polishing;
   receiving light from said surface to obtain said measurement;
   determining the results of said polishing based upon said measurement; and
   adjusting and repeating said polishing if the results of said polishing deviate from a desired result,
   wherein said second substance is provided in a vortex.

* * * * *